March 2, 1948. P. J. SCHMIDT Plant Pat. 786

BUDDLEIA PLANT

Filed Dec. 6, 1946

WITNESS

Addison F. Avery

INVENTOR

PAUL J. SCHMIDT

BY Oberlin & Limbach

ATTORNEYS.

Patented Mar. 2, 1948

Plant Pat. 786

UNITED STATES PATENT OFFICE

786

BUDDLEIA PLANT

Paul J. Schmidt, Youngstown, Ohio, assignor to The Wayside Gardens Company, Mentor, Ohio, a corporation of Ohio Application December 6, 1946, Serial No. 714,442

1 Claim. (Cl. 47—60)

Figure 1:
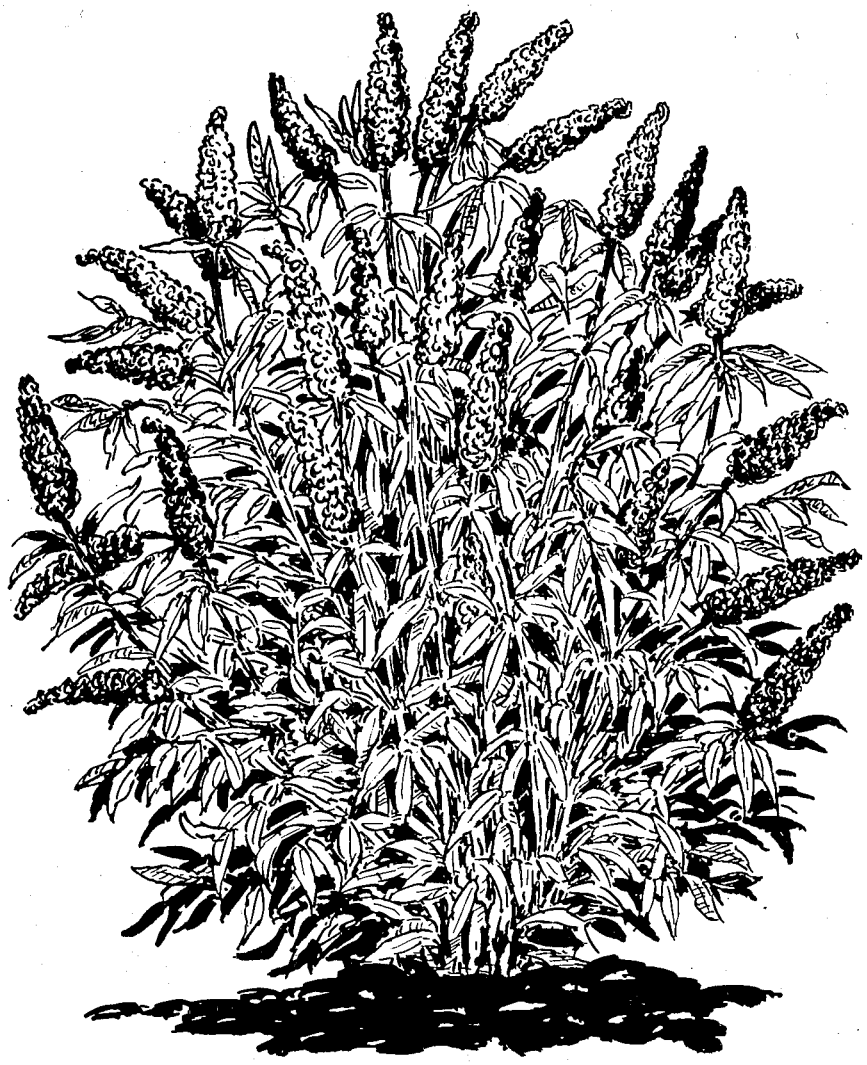

This invention relates to a new variety of buddleia plant.

In United States Plant Patent No. 705, issued to me on July 21, 1946, there is disclosed a buddleia plant characterized particularly in the large well rounded and sharp pointed flower heads composed of florets of a high degree of purity of whiteness.

The present buddleia plant is a relative of the buddleia plant therein disclosed and while having several features in common therewith has other new and distinctive features and characteristics as will more fully appear hereinafter.

The present buddleia plant was produced by me, as was the buddleia plant described in my United States Plant Patent No. 705 by crossing a white seedling buddleia plant as the female or seed parent and Buddleia Orchid Beauty as the male, or pollen, parent, Orchid Beauty being a fixed commercial variety. The white seedling, which was the female or seed parent, resulted from a cross of a white sport of the Buddleia Dubonnet and a white sport of Buddleia Fortune, the latter of which is described in U. S. Plant Patent No. 206.

The seeds resulting from this crossing of the seed and pollen parents above described were planted and from the resultant plants a number were selected for further propagation. Among those so selected were the variety of buddleia plant described in Plant Patent No. 705 and the variety of buddleia plant herein described, both of the plants thus having been produced from the seeds of the same crossing.

The present plant was asexually reproduced by root cuttings, particularly in test fields at Mentor, Ohio, and Youngstown, Ohio.

*The drawing*

The figure is a general side elevation on a reduced scale showing the general shape and branching characteristics of the plant and the manner in which the inflorescenses are borne on the terminals of the main stalks and on the laterals.

*The plant generally*

The plant has openly branched roots of the average size and is deep rooted with a lateral spread that is usual or somewhat greater than usual for buddleia plants. The roots are exceptionally resistant to disease, wetness and drouth. They also have a good winter resistance having withstood without protection temperatures as low as 4° F. below zero in Northern Ohio. The plant grows well in any good soil where winter drainage is good and thrives in soils which vary from clay loams to slightly sandy, providing the soils are moist and well drained. It requires little or no winter protection, and prefers full sun and any exposure other than a northern exposure. Though it grows well in very sandy soils, the inflorescences are smaller. In these respects the plant is substantially the same as that described in Plant Patent No. 705.

The main stalks grow upright and are very stiff and especially straight and each supports a large terminal inflorescence. However, the height of the main stalk and of the plant as a whole averages from two and one-half to three and one-half feet and thus is somewhat dwarfed and less in height than the buddleia plant of my above identified patent.

One characteristic of the present plant is that the lateral branching is quite regular, the laterals of each group being spaced 120° from the others of that group about the axis of the main stalk. The laterals of each group are positioned about the axis of the main stalk about 60° from the laterals of the groups adjacent thereto. The groups of laterals are spaced about two and one-half to three inches apart lengthwise of the main stalk. In general the laterals extend at an angle of about 40° to 45° to the axis of the main stalk and tend to curve upwardly toward their outer ends so that the flower heads on each lateral are borne in a more nearly upright position.

In general, one terminal inflorescence is borne on each lateral though infrequently one or more sub-laterals occur near the terminal of the main lateral and each sub-lateral bears a small inflorescence. The laterals vary from about ten inches in length near the top to about twenty-two to twenty-four inches near the base.

As a result of this arrangement of main stalks and laterals, the plant is branched to a high degree which is very unusual in buddleias and, as a whole, is globular and compact though somewhat elongated, having a spread about equal to or slightly less than its height.

The foliage is relatively compact, the leaves being oppositely arranged and most of the leaves being on the laterals with occasional leaves oppositely arranged on the main stalks. The leaves are somewhat shorter and narrower than those of the buddleia plant described in my above identified Patent No. 705, averaging in general from about five to six inches in length and from seven eighths to one and one half inches in width, the larger leaves generally being near the base of the plant.

The main stalks and laterals are generally uniform in color, being generally the same as the plant in said patent. The leaves on the upper surface are green comparable to Maerz and Paul Plates 23–L–7 and 8 and on the under surface are a silvery green comparable to Maerz and Paul Plate 20–A–2. They are well pointed and smooth on the upper surface and fuzzy on the under surface.

In color, the inflorescences are essentially the same and in fact are indistinguishable from the inflorescences of the plant of my above identified patent. Their size, however, is considerably different. The terminal inflorescences of the main stalks have an average length of from eight and one half to nine inches with a diameter of from one and one quarter to two inches. In general, the inflorescences taper very slightly from their bases toward their ends for about two thirds of their length and then taper more abruptly therebeyond to the end which is pointed. The lateral inflorescences are in general of the same shape as the terminal inflorescences but average from four and one half to six and one half inches in length and about an inch and a half in diameter. The number of inflorescences for each main stalk and its laterals range from fifteen to thirty, the average being about twenty-five. Two-year-old plants have been found to average about five main stalks so that the total number of inflorescences per plant is one hundred or more.

The blooming period is from about the middle of July until October or the first heavy frost, the plant blooming continuously during this period. The tendency is to bloom first at the top of the plant, the lower inflorescences blooming progressively as the season progresses but there are sufficient blooms on the plant at one time to provide good coverage.

The florets of each inflorescence first bloom near the base of the inflorescence and progressively outwardly toward the tip, but the florets near the base of each inflorescence usually remain in bloom in good condition for a sufficiently long period for all florets to be in bloom and in good condition for a while concurrently on a given inflorescence before those near the base begin to discolor.

The flowering characteristics and the color and size are affected somewhat by the usual factors of moisture, temperature and type of soil. However, the flower heads generally are filled out well entirely around the stem and are in general straight and borne substantially upright or coaxially with the terminals of the laterals on which they are borne. Their permanency on the plant is very good, most of the blooms remaining in good condition for a week on the plant. The individual florets are about the same size, shape and color as those of the buddleia plant described in my Plant Patent 705. The fragrance likewise is about the same.

Due to its dwarf size and more compact and globular shape, the present plant is well suited for planting as a midsummer shrub in front of conventional shrub borders or for mixing through perennial borders. Its advantages in this respect are enhanced by the fact that it provides a mass of blossoms during a period when practically no other flowering shrubs are in bloom.

The plant is characterized particularly in the compact arrangement of the florets, the larger number of inflorescences which are borne on each plant, the arrangement and distribution of the laterals and the dwarfed growth of the plant which results in a compact, bushy and generally globular buddleia plant, and the fact that it blooms during a period when few or no other flowering shrubs are in bloom.

I claim.

The new and distinct variety of buddleia plant herein shown and described, characterized particularly by the compact arrangement of the florets in the flower heads, the dwarfed growth, compact, bushy and globular shape of the plant as a whole, and further characterized in the very large number of inflorescences well proportioned to the size and shape of the plant as a whole, and the fact that it blooms during a period when few or no other flowering shrubs are in bloom.

PAUL J. SCHMIDT.